United States Patent [19]

Schäfer et al.

[11] 4,165,434
[45] Aug. 21, 1979

[54] LASER DYES COMPRISING FLUORESCENT AND LASER DYESTUFF RESIDUES

[75] Inventors: Fritz P. Schäfer; Wolfgang Lüttke, both of Göttingen-Nikolausberg, Fed. Rep. of Germany

[73] Assignee: Max-Planck-Gesellschaft zur Forderung der Wissenschaften e.V., Göttingen, Fed. Rep. of Germany

[21] Appl. No.: 802,337

[22] Filed: Jun. 1, 1977

[30] Foreign Application Priority Data

Dec. 6, 1976 [DE] Fed. Rep. of Germany ....... 2655177

[51] Int. Cl.² .................. C07C 15/00; C07D 251/30; C07D 251/54; C07D 311/82
[52] U.S. Cl. .................. 544/197; 260/144; 260/152; 260/153; 260/335; 260/336; 252/301.17; 331/94.5 R; 544/198; 544/216; 585/26; 585/320; 585/422; 585/469
[58] Field of Search ............ 260/144, 335, 336, 668 F; 252/301.17; 331/94.5; 544/197, 198, 216

[56] References Cited

U.S. PATENT DOCUMENTS

| | | | |
|---|---|---|---|
| 3,205,257 | 9/1965 | Fritz et al. ............... | 260/465 |
| 3,609,194 | 9/1971 | Gerhardt ................. | 260/335 X |
| 3,649,696 | 3/1972 | Kazan ..................... | 260/335 X |
| 3,798,566 | 3/1974 | McColgin et al. ...... | 260/240 R X |
| 3,859,254 | 1/1975 | Hamb et al. ............ | 260/49 |
| 3,873,940 | 3/1975 | Drexhage ................ | 260/286 R |
| 3,879,678 | 4/1975 | McColgin et al. ...... | 260/240.2 |
| 4,006,158 | 2/1977 | Fleck et al. ............. | 260/308 B |
| 4,035,740 | 7/1977 | Schafer et al. .......... | 252/301.17 X |
| 4,044,146 | 8/1977 | Karpati et al. .......... | 260/335 X |

OTHER PUBLICATIONS

Drexhage (II), J. Res. Nat. Bur. Stand, (A. Physics and Chemistry), vol. 80A, No. 3, pp. 421 to 428 (1976).

*Primary Examiner*—Floyd D. Higel
*Attorney, Agent, or Firm*—Sprung, Felfe, Horn, Lynch & Kramer

[57] ABSTRACT

Novel dyestuffs comprising at least one laser dyestuff radical and at least one fluorescent dyestuff radical, where the fluorescent range of the fluorescent dyestuff radical overlaps the absorption range of the laser dyestuff radical and is linked with the laser dyestuff radical directly or via a bridge member having a length of at most 20 Å in such a manner that the $\pi$ electron systems of the individual radicals are decoupled, are outstandingly effective and long lived when used in dyestuff lasers. The dyestuffs can be of the formula:

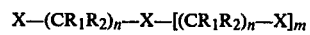

$$X\text{—}(CR_1R_2)_n\text{—}X\text{—}[(CR_1R_2)_n\text{—}X]_m$$

wherein
n is 0 or an integer from 1 up to a number corresponding to a chain length of 20 Å,
m is 0, 1, 2 or 3,
X is a laser dyestuff radical L or a fluorescent dyestuff radical F and
$R_1$ and $R_2$, which can be the same or different, are hydrogen or alkyl of up to 6 carbon atoms,
with the provisos that one of the groups X is a laser dyestuff radical L, all the fluorescent dyestuff radicals F can be the same or different and the bridge members $CR_1R_2$ can also be joined together by oxygen, nitrogen, or sulfur.

9 Claims, No Drawings

LASER DYES COMPRISING FLUORESCENT AND LASER DYESTUFF RESIDUES

The present invention is concerned with new dyestuffs and with the preparation thereof. More particularly, the invention relates to new dyestuffs having substantially greater effectiveness and longer life when used in dye lasers.

Of the laser dyestuffs conventionally employed, only a small fraction of white excitation light of the xenon flash light normally employed as source of excitation light can be utilized. This fraction is preponderantly that absorbed by the narrow longwave bands of the dyestuff molecule. Since the half-width of the absorption bands of the conventional laser dyestuffs typically amount to 5000 cm$^{-1}$ and the emission spectrum of the xenon flash lamps extends from the permeability limit of the quartz glass bulb at about 200 nm (50,000 cm$^{-1}$) to above the absorption limit of the longest wave-absorbing dyestuffs at about 1 μm (10,000 cm$^{-1}$), i.e. covers 40,000 cm$^{-1}$, usually there can only be utilized about one eighth of the available capacity of the exciting xenon flash lamp. In fact, the utilized fraction is usually very much smaller since, in fact, the energy emitted by the xenon flash bulb is not uniformly distributed over the whole spectrum but rather increases considerably in the direction of the short wavelengths. This effect becomes more pronounced as the current increase velocity of the current impulse through the flash lamp becomes higher and the current density therein becomes greater. Since, for reasons which are well known in the art, in the usual dye lasers not only the current increase velocity but also the current density is selected to be as high as possible, usually only about one tenth of the light radiated in can be absorbed and converted into laser beams. Due to this and due to the losses in the case of the conversion of electrical into optical energy in the flash lamp, there is given a maximum degree of action (laser energy/electric impulse energy) of only 1.5% in the case of the best dye lasers which today exist. A more detailed discussion of the matter is given by F. P. Schäfer: "Principles of Dye Laser Operation" in "Dye Lasers", ed. F. P. Schäfer, pub. Springer-Verlag, Berlin, Heidelberg, New York, 1973.

The present invention provides new dyestuffs and processes for the preparation thereof which utilizes the greatest possible function of the light of excitation and thereby achieve a higher degree of action of the dye laser.

The present invention also provides dyestuffs which make it possible to operate dye lasers in impulse operation not only with xenon flash lamps but also with the use of continuously burning, incoherent sources of light with an essentially white spectrum, for example xenon high pressure lamps, metal halide lamps or the sun, the intensity of which, in the case of using conventional dyestuffs, is not sufficient for the continuous operation of dye lasers.

Use of the present invention also increases the period of life of laser dyestuffs. It is known that all dyestuffs are destroyed photochemically more or less quickly, which is essentially brought about by the ultra-violet component of the excitation light. Thus, for example, the period of life of a solution of Rhodamine 6G in a dye laser described by L. Ringwelski and F. P. Schäfer (see F. P. Schäfer, "Liquid Lasers", in Laser Handbook, ed. F. T. Arecchi and E. O. Schulz-Du Bois, pub. North-Holland, Amsterdam, 1972, p. 404) could be increased tenfold by filtering out the ultra-violet component of the excitation light through a 0.75 molar solution of copper sulphate.

Further, the invention provides new dyestuffs for textiles, leather and the like, as well as pigment dyestuffs for coating paints, lacquers, printing dyes and the like which have a superior light fastness.

Attempts have already been made to better utilize the excitation light spectrally by using, instead of a single laser dyestuff, mixtures of the laser dyestuff with shorter wavelength absorbing dyestuffs with good fluorescence, the fluorescence of the admixed dyestuff being partly absorbed by the laser dyestuff, the excitation energy in the laser dyestuff thereby being effectively increased (see British patent specification No. 1,255,399). However, the increases mentioned therein of the output energy of the dye laser after the addition of the fluorescent dyestuff are not a measure for the better utilization of the excitation light but merely a purely random manipulatable measurement number which can be shown by the following considerations. In Example 3 of the above-mentioned British patent specification, in a dye laser there is used acridine red as laser dyestuff at a concentration of 10$^{-4}$ M and a particular laser energy measured at a condenser voltage of 15 kV. Rhodamine 6G is then added thereto as fluorescent dyestuff until the solution is 10$^{-4}$ M with regard to both dyestuffs and an increase of the laser energy by a factor of 9.5 is measured. If the condenser voltage is now lowered to such an extent that, with the pure acridine red solution, one just remains somewhat below the threshold of the laser emission and then, at the same voltage, uses the mixture, then there would be measured a particular laser energy since now, due to the additional increase of the excitation energy of the acridine red achieved by the fluorescence of the rhodamine, one would go above the laser threshold which would mean an increase of the output energy by a factor of infinity. Thus, by corresponding adjustment of the condenser voltage between the threshold value for the laser emission and 15 kV, there can now be achieved every factor between infinity and 9.5 and also, by further increase of the condenser voltage, the factor will be below 9.5. A substantially better measurement value for the improvement of the degree of action has been suggested by W. Schmidt, W. Appt and N. Wittekind in Z. Naturforsch., A27, 37/1972 by measuring the electrical impulse energy at which a particular laser energy is achieved with the laser dyestuff alone and then determining with the mixture the electrical impulse energy at which there is achieved the same laser energy as with the laser dyestuff alone. The ratio of the two electrical energies is a very good measurement value for the achieved improvement of the utilisation of the excitation light spectrum. The last-mentioned authors (loc. cit.) found that, in their dye laser with cresyl violet, the excitation energy, in order to obtain 10 KW laser power, was lowered by a factor of 2 when, as fluorescent dyestuff, an optimum amount of rhodamine 6G was added to the solution and that, at a laser power of 25 kW, this factor amounted to 2.7.

The above-described known process of improving the degree of action of the laser by mixing fluorescent and laser dyestuffs nevertheless possesses serious disadvantages. Thus, in the case of the concentrations which are usually employed in the case of dye lasers excited with flash lamps, which, as a rule, are <10$^{-4}$ M, the energy transmission from the fluorescent dyestuffs to the laser dyestuff is by no means complete. A greater part of the fluorescent light emitted isotropically in all directions is thus lost through the walls of the cuvette instead of being usefully resorbed by the laser dyestuff molecules insofar as the energy transfer takes place by radiation. However, the energy transfer from the fluorescent dyestuff (donor) to the laser dyestuff (acceptor) can also take place without radiation. The probability for this can be calculated according to the theory of Th. Förster, "Fluoreszenz organischer Verbindungen", pub. Gottingen, 1951, p.83). The characteristic distance $R_o$ between donor and acceptor molecules at which the probability for the radiationless energy transfer amounts to 50%, is, in the case of good spectral overlapping of the fluorescent bands of the donor molecule with the absorption bands of the acceptor molecule of the order of magnitude of 100 Å, whereas the average molecule distance in the case of the given concentration amounts to about 200 Å. Only in the case of very high concentrations which are needed in the case of the excitation of the dye laser with the help of nitrogen lasers or other lasers can there be achieved an almost complete radiationless, energy transfer, which has been demonstrated by I. B. Berlman, M. Rokni and C. R. Goldschmidt (Chem. Phys. Lett., 22, 458/1973) but is without importance for the present problem of exciting the laser with an incoherent white source of light.

An even more serious disadvantage is, however, the fact that the excited donor molecules frequently display new absorption bands in the excited state which lie precisely within the spectral range of the laser emission and thus reabsorb the laser light and thereby lower the laser capacity or even completely suppress the laser emission. Such examples are given by W. Schmidt et al. (loc. cit.), as well as by A. Hirth (Thesis, Strasbourg, 1974, p.90) where the laser dyestuff hexamethylindotricarbocyanine, after the addition of various fluorescent dyestuffs, for example, rhodamine 6G, cresyl violet, diethyloxatricarbocyanine or oxazine 1 of Eastman Kodak, always shows a reduction of the laser energy when referred to the laser dyestuff used alone. Hirth was able to show that this reduction of the laser energy was brought about by new absorption bands of the excited fluorescent dyestuff by utilising double-walled cuvettes in the inner vessel of which was the laser dyestuff and in the outer concentric mantle vessel of which was one of the abovementioned fluorescent dyestuffs. In all of these cases, there was an increase of the laser energy since the fluorescent radiation emitted from the fluorescent dyestuff was at least partly absorbed by the inner cuvette with the dyestuff solution and thus increased its excitation energy without, at the same time, an absorption being introduced into the laser beam running along the axis of the cuvette and filling the inner cuvette. The increase of the laser energy was thereby only moderate (about 50%) since the greater part of the fluorescent light from the outer mantle cuvette went past uselessly on the inner cuvette.

The above-described disadvantages are wholly or at least partly overcome by the present invention.

Thus, according to the present invention, there are provided dyestuffs based on at least one laser dyestuff molecule, which are characterised in that they contain at least one fluorescent dyestuff molecule residue, the fluorescent range of which overlaps with the absorption range of the laser dyestuff molecule residue and which is attached to the laser dyestuff molecule residue directly or via a bridge member with a length of at most 20 Å in such a manner that the $\pi$-electron system of the individual laser dyestuff and fluorescent dyestuff molecule residues do not form a common conjugated system capable of mesomerism.

This attachment can consist of mesomerism-inactive bridge members, for example —$(CH_2)_n$— groups of at most 20 Å length, spiro atoms or linkages via aromatics at points which are substantially or completely mesomerically inactive, such as benzene derivatives in the m-position to one another. Furthermore, the subunits comprising the dyestuffs can also be joined together directly but, by means of appropriately arranged, sufficiently voluminous substituents, strongly twisted with regard to one another and prevented from forming an overall coplanar system.

The solution, according to the present invention, of the problem of providing new laser dyestuffs with a higher degree of action and a longer period of use and a process for the preparation thereof starts initially from known dyestuffs. The term "dyestuff" is here used in the wider sense in that there is meant all substances with conjugated double bonds, which includes the dyestuffs in the limited sense of materials which absorb visible light. Initially, there is selected a laser dyestuff L which emits in the desired wavelength range. A laser dyestuff is, in the scope of the present invention, defined as a dyestuff in the wider sense (i.e. light absorption by excitation of a $\pi$-electron) which possesses a sufficient quantum yield, i.e. more than 0.5 of the fluorescence, and the singlet-singlet absorption of which ($S_1$–$S_n$) is smaller than the stimulated fluoresence emission cross-section. A fluorescent dyestuff $F_1$ is then selected, the fluorescent band of which should overlap as much as possible with the absorption bands of the laser dyestuff. Further criteria for the selection of a suitable fluorescent dyestuff are explained hereinafter. Further fluorescent dyestuffs $F_2$, $F_3$, $F_4$ and so forth can now be selected which can be the same or different insofar as the particular absorption bands of the dyestuff with the smaller index and the fluorescent bands of the dyestuff with the higher index overlap as much as possible. According to the present invention, the dyestuffs thus selected are now joined together by chemical bonds either directly or via bridge members in such a manner that the spatial distance of the points of attachment of the dyestuffs amounts to, at most, about 20 Å but the dyestuffs are attached in such a manner that the $\pi$-electron systems of the neighbouring dyestuffs are decoupled and thus no substantial changes occur in the absorption spectra in comparison with the non-bound dyestuffs. In other words, no mesomerism is to occur between the mesomeric systems of the individual dyestuff molecules. As will be readily appreciated, this chemical linking of the dyestuffs can take place according to well known methods, some of which will be mentioned hereinafter, by way of example. On the basis of the given examples, further analogous methods of linking can be worked out. It will also be immediately recognised that, from case to case, one will either start from the dyestuff molecules to be linked themselves, react the first of these with one of the end groups of a linking molecule and then react the other end group with the second dyestuff molecule; or, in other cases, instead of starting from the unchanged dyestuff molecule, to start from unsubstituted dyestuffs or from dyestuff derivatives substituted with appropriate reactive groups or from pre-products of such dyestuffs which form the desired dyestuff in the course of the linking reaction or reactions.

Even with the chemically easily produced linear linkage by two methylene groups, there are provided numerous possibilities for linking, the new laser dyestuffs being constructed, for example, according to the following scheme:

L—CH$_2$—CH$_2$—F$_1$, L—CH$_2$—CH$_2$—F$_1$—CH$_2$—CH$_2$—F$_2$, L—CH$_2$—CH$_2$—F$_1$—CH$_2$—CH$_2$—F$_2$—CH$_2$—CH$_2$—F$_3$ and so forth; or F$_1$—CH$_2$—CH$_2$—L—CH$_2$—CH$_2$—F$_2$ or F$_1$—CH$_2$—CH$_2$—F$_2$—CH$_2$—CH$_2$—L or F$_1$—CH$_2$—CH$_2$—L—CH$_2$—CH$_2$—F$_3$ or
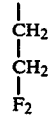

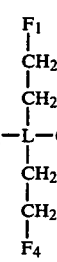
F$_2$—CH$_2$—CH$_2$—L—CH$_2$—CH$_2$—F$_3$ or

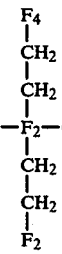
F$_3$—CH$_2$—CH$_2$—F$_2$—CH$_2$—CH$_2$—L and, corresponding to these examples, further combinations. Instead of the linking via two methylene groups which, inter alia, is especially easy to carry out, linking can, of course, also take place via one or more than two methylene groups. Furthermore, instead of the two methylene groups, there can also be used —CHR— or —CR$_1$R$_2$— groups, as well as —CH$_2$—O—CH$_2$— or —CH$_2$—N(R)—CH$_2$— or —CH$_2$—S—CH$_2$— groups.

According to a preferred embodiment of the present invention, there are provided dyestuffs of the general formula:

X—(CR$_1$R$_2$)$_n$—X—[(CR$_1$R$_2$)$_n$—X]$_m$ in which n is 0 or a whole number from 1 up to a number corresponding to a chain length of 20 Å, m is 0, 1, 2 or 3, X is the residue of a laser dyestuff L or the residue of a fluorescent dyestuff F and R$_1$ and R$_2$, which can be the same or different, are hydrogen atoms or alkyl groups containing up to 6 carbon atoms, with the proviso that one of the groups X represents a residue of L, all the residues F can be the same or different and the bridge members CR$_1$R$_2$ can also be joined together by oxygen, nitrogen or sulphur atoms. When the groups —(CR$_1$R$_2$)$_n$— are only alkylene groups, then n is a number of up to 13.

Another method of linking is one in which three dyestuffs are linked via a tertiary carbon atom, provided that the steric relationships permit this. Examples of this include the following:

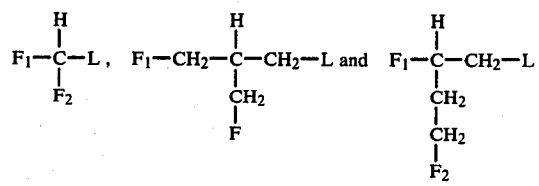

and corresponding further variations. They can be represented by the general formula:

HC—[(CH$_2$)$_n$X]$_3$ wherein n and X have the same meanings as above.

Yet another method of linking is via one or more quaternary carbon atoms, for example in a spiro or allene system, which is possible, for example, in the manner represented by the following general formula:

Still a further method of linking is in the manner of the cyclophanes, as illustrated by the following formulae:

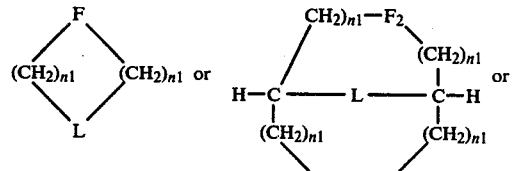

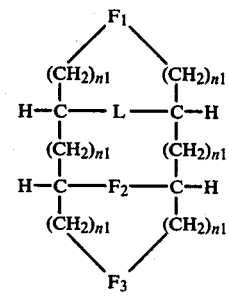

and so forth. In the case of these general formulae, n1 is a whole number of from 1 to 13 and preferably of from 1 to 4.

Cyclic or mesh-like arrangements or also layer-like arrangements with cross-linkages can also be constructed.

Furthermore, the dyestuff residues X can also be side chains of cyclic compounds, in which case they can be arranged on the ring not only in neighboring positions but also spaced apart from one another. The following general formula illustrates one possibility, by way of example:

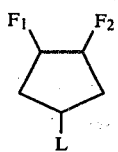

Dyestuffs linked according to the present invention in this manner via an alicyclic or heterocyclic ring system can be obtained, for example, by 1,3-dipolar addition or by Diels-Alder or other cyclo-additions.

Furthermore, hetero atoms can also be introduced into the bridges or can be used as bridges, for example an ether bridge, such as is illustrated by the following general formula:

$$F_1-CH_2-O-CH_2-L-CH_2-O-F_2$$

and so forth.

Furthermore, two dyestuffs can be linked together directly without bridge atoms without the $\pi$-electron systems thereby mutually influencing one another, in that these either because of their structural characteristics of themselves or due to the introduction of sufficiently space-filling substituents on at least one of the dyestuffs provide that the planes of the dyestuffs stand substantially orthogonal to one another.

The dyestuffs can also be linked via unsaturated or aromatic or heterocyclic groupings when the above-mentioned conditions are fulfilled which are necessary for the isolation of the chromophores, for example steric conditions. To this also belongs a mesomerically substantially indifferent linkage via an aromatic molecule, for example by meta linkage via a benzene ring, as illustrated by the following general formula:

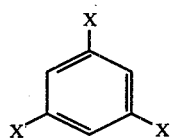

in which X has the same meaning as above.

The linkage of the dyestuffs is, when they each carry at least one hydroxyl or amino group, also possible via molecules such as cyanuric chloride or other anchor compounds which can be used for the construction of reactive dyestuffs, for example, as illustrated by the following general formulae:

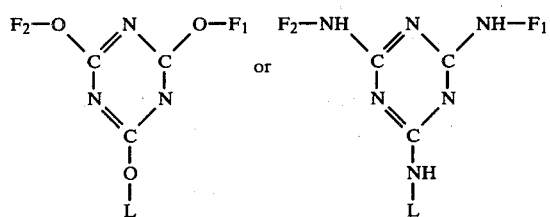

Numerous methods are available for the preparation of the new dyestuffs according to the present invention. Especially simple is the linkage of the various dyestuff residues X with the help of bridge-building compounds with two reactive groups which can produce the linkage with the dyestuff residues. Examples of bridge-building compounds include diols, dialdehydes, dicarboxylic acids and reactive derivatives thereof, for example, esters, acid chlorides, acid azides, isocyanates and the like; and diepoxides, diamines and the like. These bridge-building compounds can be reacted with appropriate reactive groups in the individual dyestuff molecules in known manner, for example, with carboxyl groups and derivatives thereof, amino groups, hydroxyl groups, keto groups, aldehyde groups and the like. All these reactions are well known and do not need to be described here in detail (see E. Siegel: Reactive dyes: reactive groups in: K. Venkataraman, The Chemistry of Synthetic Dyes, Vol. 6, 1-209/1972; as well as Coons, J. Immunology, 45, 149/1942 and Riggs, Am. J. Pathol., 34, 1081/1958).

Typical examples of the above-mentioned reactions include the reaction via a carboxyl group or activated carboxyl group present in the dyestuff molecule with a diol with the formation of the corresponding hemiester which is then reacted with a second dyestuff molecule to give a dyestuff according to the present invention. This reaction can be carried out, for example, in the presence of a strong acid in a water-immiscible organic medium, for example a halogenated hydrocarbon. Examples of strong acids which can be used for this purpose include sulphonic acid, such as toluene-sulphonic acid, or polymers containing sulphonic acid groups.

Another possibility for linking the carboxyl group with a hydroxyl group involves carrying out the reaction in the presence of an alcoholate.

If the dyestuff residue to be incorporated into the dyestuff according to the present invention does not contain any reactive substituents but does contain an aromatic system, then it is possible to produce the linkage by means of the methods of aromatic substitution. For example, phenyl groups can be substituted with activated acid derivatives, such as acid anhydrides or acid chlorides, in the presence of aluminium chloride, in an appropriate organic medium. The ketones thus formed can, in turn, be reduced in known manner, with the removal of the oxygen atom, for example with hydrazine hydrate in a strongly alkaline medium.

A further possibility of linking dyestuffs X which contain a hydroxyl or amino group is the reaction with cyanuric chloride, with the formation of an s-triazine, for example according to the following reaction scheme:

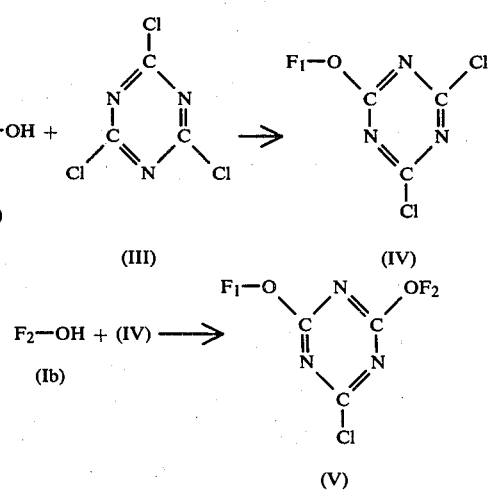

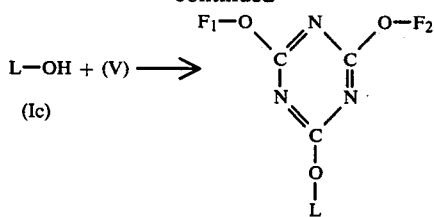

According to a further method of linking, each of the dyestuffs $F_1, F_2 \ldots$ and L is provided with a reactive group R. These dyestuffs are then linked with an appropriate polyalcohol, polyphenol or polyamine (or also with mixed aminoalcohols) to give a dyestuff according to the present invention with, for example, the following mode of construction:

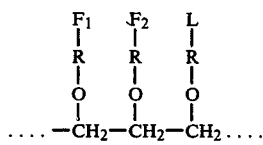

Of course, two or more of the described methods of linking can be combined with one another if it appears reasonable to do so under the particular circumstances, especially having regard to the chemical properties of the dyestuffs to be linked together.

Consequently, the process according to the present invention for the preparation of the above-described new dyestuffs consists in that, in known manner:

(a) a first laser dyestuff or fluorescent dyestuff carrying, inter alia, a reactive group, is reacted with a bridge-building compound, the molecule length of which does not substantially exceed 20 A and which contains at least two reactive groups, at least one of which is able to form a covalent bond with the first dyestuff, in equimolar amounts and the reaction product with its second reactive group is reacted with a second dyestuff which differs from the first dyestuff, one of the dyestuffs being a laser dyestuff, and the product is, if desired, reacted one or more times with a further bridge-building molecule and a further fluorescent dyestuff, or (b) an aromatic ring system is reacted, under the conditions of meta substitution, with at least one fluorescent dyestuff and with a laser dyestuff which carry groups capable of substitution, for example, activated acid residues, or (c) a laser dyestuff and at least one fluorescent dyestuff are reacted with an appropriate anchor molecule, for example, a cyanuric halide, or (d) a laser dyestuff and at least one fluorescent dyestuff are linked directly with one another by methods conventionally used for the preparation of corresponding aromatic compounds, the formation of a common conjugated system being prevented by means of sufficiently voluminous substituents, or (e) a laser dyestuff and at least one fluorescent dyestuff are each linked with a bifunctional bridge-building molecule, the second reactive group of the bridge-building molecule being subsequently linked with a common anchor molecule, which can be an aromatic hydrocarbon, a heterocycle or a high molecular weight polymer.

In the case of the new dyestuffs, the difficulty sometimes arises that, because of the size of the molecule, the solubility in water or in an alcohol, which are the most used solvents for laser dyestuffs, is too low. This difficulty can be avoided when, in known manner, into the molecular structure there are introduced groups which improve the solubility, for example, sulphonate groups or quaternary amino or alkylamino groups for increasing the solubility in water and/or straight-chain or branched alkyl radicals and/or tertiary alkylamino radicals for increasing the solubility in an alcohol.

The outstanding suitability of the above-described dyestuffs as laser dyestuffs is due to the fact that, within the molecule, a radiationless transfer of energy takes place from the residues of the fluorescent dyestuff $F_i$ ($i=1, 2, 3 \ldots$) to the residue of the laser dyestuff L in such a manner that, depending upon the degree of overlapping of the absorption and fluorescent spectra in question in the above-described manner, the transmission of energy takes place either directly to the laser dyestuff or in several stages from one fluorescent dyestuff to the other and finally to the laser dyestuff. Since, according to the present invention, the distance between the residues of the fluorescent dyestuffs and the residues of the laser dyestuff is less than 20 Å, the radiationless transfer of energy is practically complete, which can be calculated quantitatively in the following manner. The transfer rate K for the radiationless transfer of energy from the donor molecule to the acceptor molecule, for example from $F_1$ to L or from $F_i$ to $F_{i-1}$, is, according to the Forster theory, given by the equation:

$$k = 1/\tau_F (R_o/R)$$

wherein $\tau_F$ is the fluorescence lifetime of the donor molecule at infinite distance form the acceptor molecule, R is the distance between the donor molecule and the acceptor molecule and $R_o$ is a characteristic distance at which the probability of the energy transfer is just 50% and which can be calculated from the spectra of the donor and acceptor molecule and, in the case of most of the dyestuffs which can be considered, is of the order of 100 Å. In order to be able to calculate the magnitude of K, for R there is used the greatest possible distance, according to the present invention, of the points of linkage of the donor and acceptor molecules, i.e. R=20 Å. Thus, $$K = 1/\tau_F (100/20)^6 = 15625/\tau_F$$

This means that the transfer rate of the radiationless energy transfer from the donor molecule to the acceptor molecule is more than $10^4$ times greater than the deactivation of the excited donor molecule by spontaneous fluorescence emission $1/\tau_F$. Consequently, the transfer of the energy of excitation from the donor molecule to the acceptor molecule is practically complete since only less than each ten thousandth donor molecule emits spontaneously instead of transferring its energy to the acceptor molecule. If the spatial distance between the donor and the acceptor is substantially less than 20 Å, then the transfer rate K assumes even greater values. The given $R_o$ values refer, according to Forster's theory, to an average value for statistically oriented donor and acceptor molecules, whereas here there is present, inter alia, a spatial fixing together. Taking all factors into account, for all possible orientations, there is obtained a correction factor of the order of magnitude of only 1.

Thus, in the case of the dyestuffs according to the present invention, as a result of the favouring of the energy transfer, the photochemical action of the light is, without the necessity of an external filter, reduced to an immaterial fraction and thus the period of use thereof is considerably increased.

It is especially noteworthy that the energy transfer, because it takes place intramolecularly, is of unchanged effectiveness, even in the case of very dilute solutions such as are required in the case of dye lasers of large volume, in contradistinction to the radiationless energy transfer in dyestuff mixtures such as have previously been used.

A further advantageous action of the intramolecular radiationless energy transfer in the new dyestuffs is caused by the shortening of the lifetime of the excited state of the donor. Whereas the lifetime $\tau$ of the excited singlet state of the isolated donor molecule (i.e. in good approximation in solutions with concentrations of less than $2 \times 10^{-4}$ M) is the same as the fluorescence lifetime $\tau_F$, $\tau$ is shortened by the radiationless energy transfer according to the equation:

$$1/\tau = 1/\tau_F + K$$

Thus, according to the above estimation, $\tau < 10^{-4} \times \tau_F$. Since, however, the absorption probability of an excitation light quantum or (what is even more important due to the losses brought about thereby) of a laser light quantum due to an excited donor molecule is proportional to the lifetime of its excited state, the losses due to reabsorption of the excitation and/or laser light are, in the new dyestuffs, reduced by a factor of at least $10^4$ in comparison with mixtures of the corresponding dyestuffs. In fact, this factor is substantially greater since the number of the long-life triplet states with an absorption probability which, according to their long lifetime of typically more than $10^{-7}$ seconds, is especially high, is reduced because the number of triplets produced is also proportional to the lifetime of the excited state.

From the statements concerning the shortening of the lifetime of the excited state by radiationless energy transfer, it can also be immediately assumed that even practically non-fluorescing donor molecules can be used since the radiationless deactivating processes competing with the radiationless energy transfer, even in the case of fluorescence quantum yields of $10^{-4}$ (i.e. in the case of "non-fluorescing" dyestuffs), are slower than the radiationless energy transfer. This has already been demonstrated experimentally by D. Möbius and G. Dreizler (Photochem. Photobiol., 17, 225/1973) using, by way of example, non-fluorescing azo dyestuffs as donor molecules and cyanine dyestuffs as acceptor molecules. Nevertheless, as donor molecules there are advantageously used those with at least moderate fluorescence quantum yields (about >1%) in order to suppress as far as possible the competing radiationless deactivation processes since they signify a loss of excitation energy, albeit small.

The prolongation of the period of life of the new dyestuffs which can be achieved according to the present invention when they are used as laser dyestuffs follows from the fact that, in the immediate proximity of the laser dyestuff residue, a shortwave radiation absorbing fluorescent dyestuff residue is situated which serves the laser dyestuff residue as a protective filter. This protective action is the greater, the more fluorescent dyestuff residues are, in the same molecule, linked in the above-described manner with the laser dyestuff residue. It could, however, be expected that then the donor molecules absorbing the ultra-violet light might possibly be photochemically destroyed and thus lose their protective action. However, we have found that the donor molecule is substantially protected against photochemical destruction by the shortened lifetime of the excited state due to the radiationless energy transfer to the acceptor molecules.

A further favourable property of the new dyestuffs is achieved when one of the fluorescent dyestuff residues linked with the laser dyestuff residues has a triplet level, the energy of which is lower than the triplet level of the laser dyestuff residue and when this fluorescent dyestuff residue is attached to the laser dyestuff residue in such a manner that the spatial distance of the points of attachment amount to only a few Ångstrom (up to about 8 Å). Furthermore, the said fluorescent dyestuff residue need not possess any or at most only a low triplet-triplet absorption in the region of the laser wavelength. The following action is thus achieved: the said fluorescent dyestuff residue absorbs excitation light and transfers its excitation energy radiationless either directly or via one or more stages to the laser dyestuff residue. This now emits either stimulated or spontaneously a light quantum or is deactivated by radiationless processes. There is thereby a certain degree of probability that the said laser dyestuff residue passes over into the triplet state which, with its long lifetime, would bring about strong reabsorption losses in the above-described manner. However, due to the proximity of the said fluorescent dye stuff residue there is, with a high degree of probability, brought about a radiationless energy transfer to its lower-lying triplet level. In this manner, the triplet state of the laser dyestuff is rapidly eliminated without additional triplet quenchers, for example, oxygen or cyclooctatetraenes, having to be added which, in most cases, also display undesired chemical side effects.

Finally, it should be mentioned that the dyestuffs here described can, of course, also be advantageous for other fields of use, for example, as textile, leather or pigment dyestuffs, for example for lacquers, paints or printing colours. Due to the linkages herein described, there can be produced especially lightfast textile dyestuffs, for example, black which does not become greenish and the like, which, by other routes, such as by dyestuff mixtures or by subsequent dyeing with one or more further dyestuffs, can only be obtained with difficulty, if at all. According to the above description, it is a simple matter, by appropriate substitution and selection of the dyestuffs to be linked, to carry out an adoption of the properties of the new dyestuffs to the particular field of use, for example the dyeing properties to various textile fibres and the like.

The following Examples are given for the purpose of illustrating the present invention:

EXAMPLES

In the following, there are described synthesis routes for three of the new laser dyestuffs and, in each case, further dyestuff combinations are mentioned which can be linked in the described manner in order to obtain new laser dyestuffs.

EXAMPLE 1

Rhodamine K1

The new dyestuff, referred to as Rhodamine K1, is formed by linking Rhodamine 6G and Rhodamine B in the following manner:

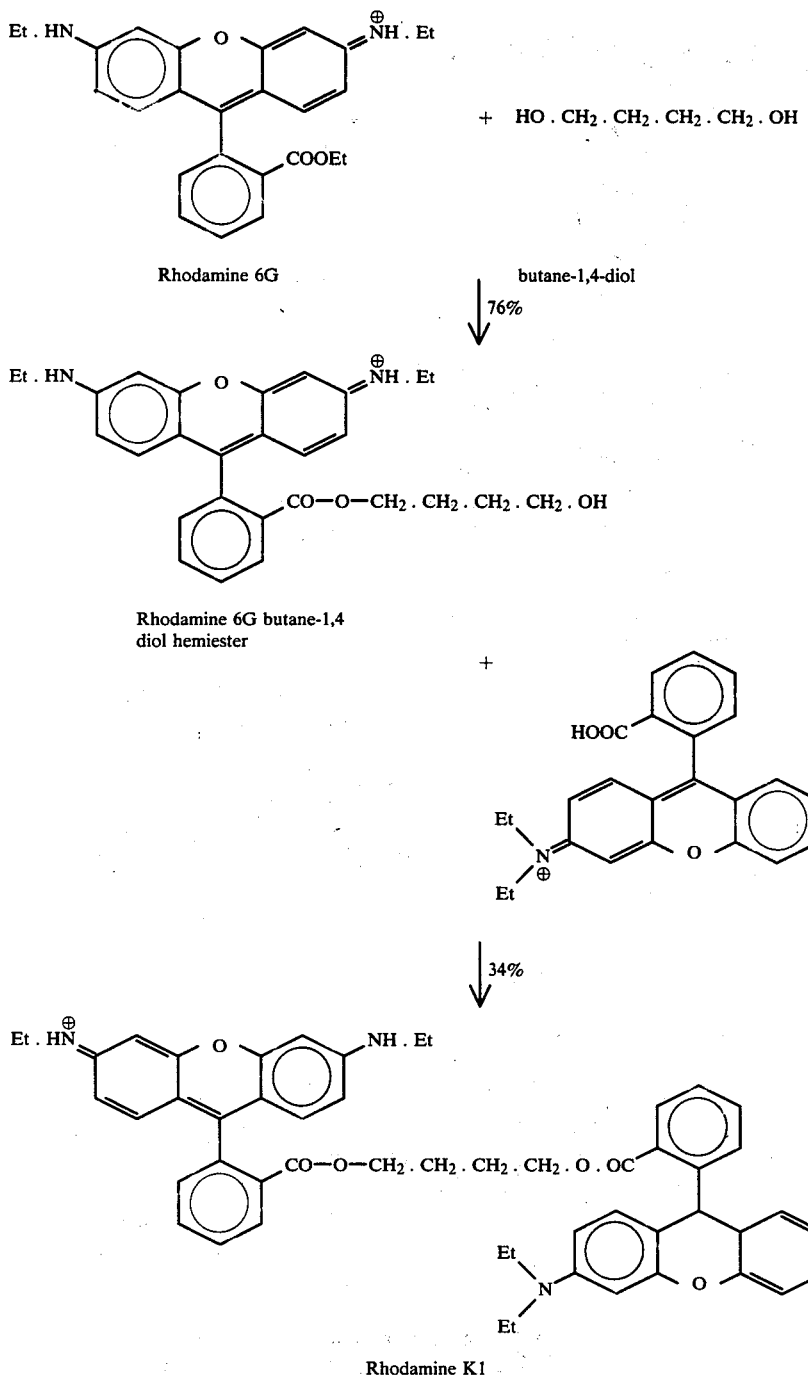

A. Rhodamine 6G butane-1,4-diol hemiester 44 g. (0.1 mol) Rhodamine 6G and 27 g. (0.3 mol) butane-1,4-diol are heated to about 100° C. with about 3 g. sodium methylate under water pump vacuum until no more ethanol distils off. While cooling, the reaction mixture is just neutralised with 10% hydrochloric acid until the hemiester of the base precipitates out. It is filtered off with suction, washed with a little cold water and dried. The yield is 35.5 g. (76% of theory).

B. Rhodamine 6G—Rhodamine B butane-1,4-diol diester (Rhodamine K1)

11.6 g. (0.03 mol) Rhodamine B are mixed with 6 g. concentrated sulphuric acid, while cooling carefully, and then 30 g. (0.06 mol) of the butane-1,4-diol hemiester of Rhodamine 6G are introduced. After leaving the reaction mixture to stand for 2 hours at ambient temperature, it is heated to 80° C. for 1 hour and the solution is then poured into 600 ml. ice water. After about 10 hours, the mass has crystallised. The mixture of sulphates is filtered off, dissolved in water and neutralised with an aqueous solution of sodium carbonate. Unreacted Rhodamine 6G and Rhodamine B are filtered off. The filtered solution is carefully salted out with a concentrated aqueous solution of sodium chloride, the hydrochloride of the diester thereby precipitating out. The yield of 9.1 g. (34% of theory).

Analogous linkings were also carried out with the following pairs of dyestuffs:
Rhodamine 6G+Rhodamine S
Rhodamine 6G+pyronine
Rhodamine S+2,7-dichlorofluorescein.

EXAMPLE 2

Fluoroscein K1

The new dyestuff, referred to as fluoroscein K1, is formed by linking fluorescein with 2,7-dichlorofluoroscein in the following manner:

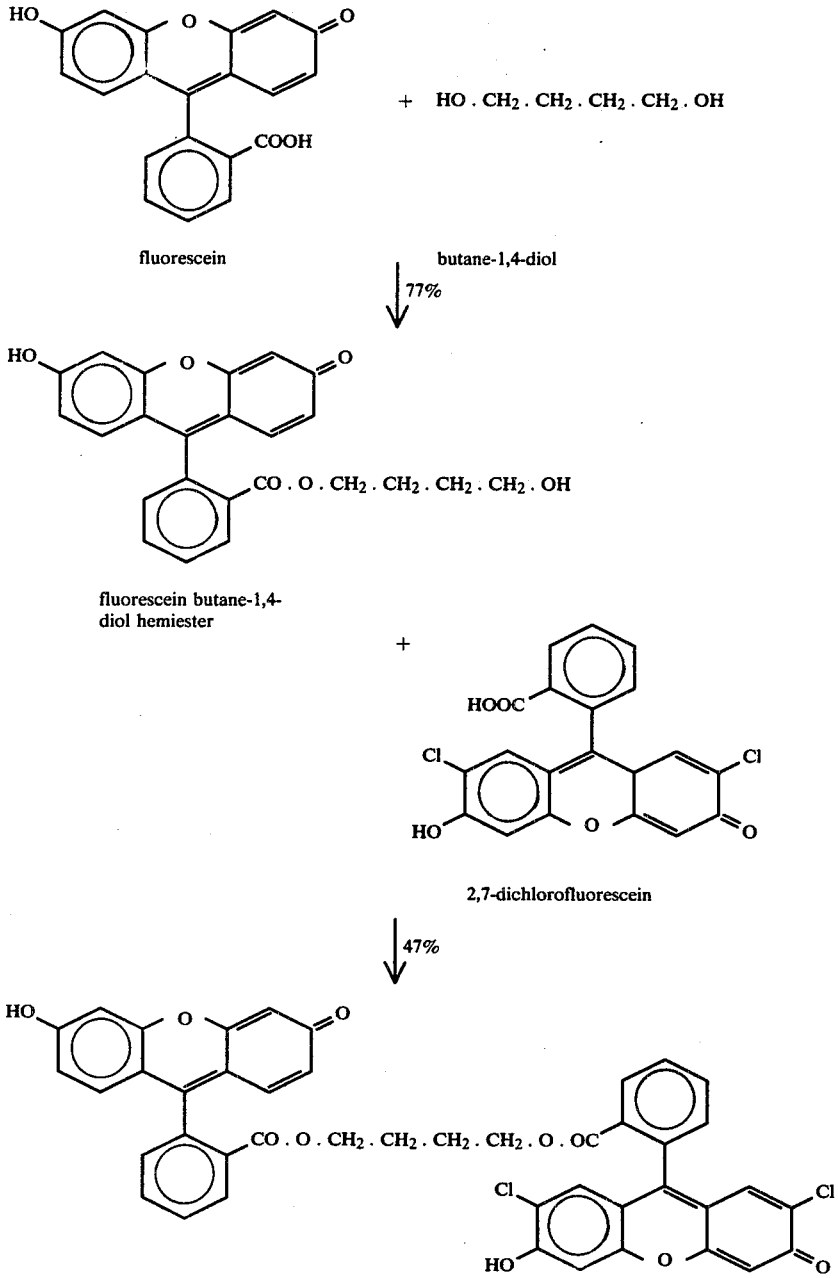

A. Fluorescein butane-1,4-diol hemiester 33.2 g. (0.1 mol) Fluorescein are mixed with 50 g. (0.6 mol) butane-1,4-diol, 2 g. toluene-sulphonic acid and 100 ml. chloroform and boiled under a water separator (8 hours) until no more water separates. The bulk of the unreacted alcohol and of the chloroform are distilled off. The precipitated product is filtered off and repeatedly washed with water, aqueous sodium bicarbonate solution and again with water. The red hemiester produced is filtered off with suction and washed first with water and then with cold ethanol. The crude product obtained is recrystallised from acetone. The yield is 31 g. (77% of theory).

B. Fluorescein-2,7-dichlorofluorescein butane-1,4-diol diester (fluorescein K1)

12.3 g. (0.02 mol) 2,7-Dichlorofluorescein are boiled for 15 hours with 24.2 g. (0.06 mol) fluorescein butane-1,4-diol hemiester and 3 g. toluene-sulphonic acid in 300 ml. glycol diethyl ether in a recycling apparatus with a separate drying agent (phosphorus pentoxide). The bulk of the solvent is then distilled off, the residue is washed with water, aqueous sodium bicarbonate solution and again with water and the solid reaction product is filtered off with suction, washed with warm water and then with ethanol. The crude product is subsequently recrystallised twice from n-butyl acetate. The yield is 7.4 g. (47% of theory).

EXAMPLE 3

Terphenyl K1

The new laser dyestuff, referred to as terphenyl K1, is formed by linking 9,10-diphenyl-anthracene and terphenyl in the following manner:

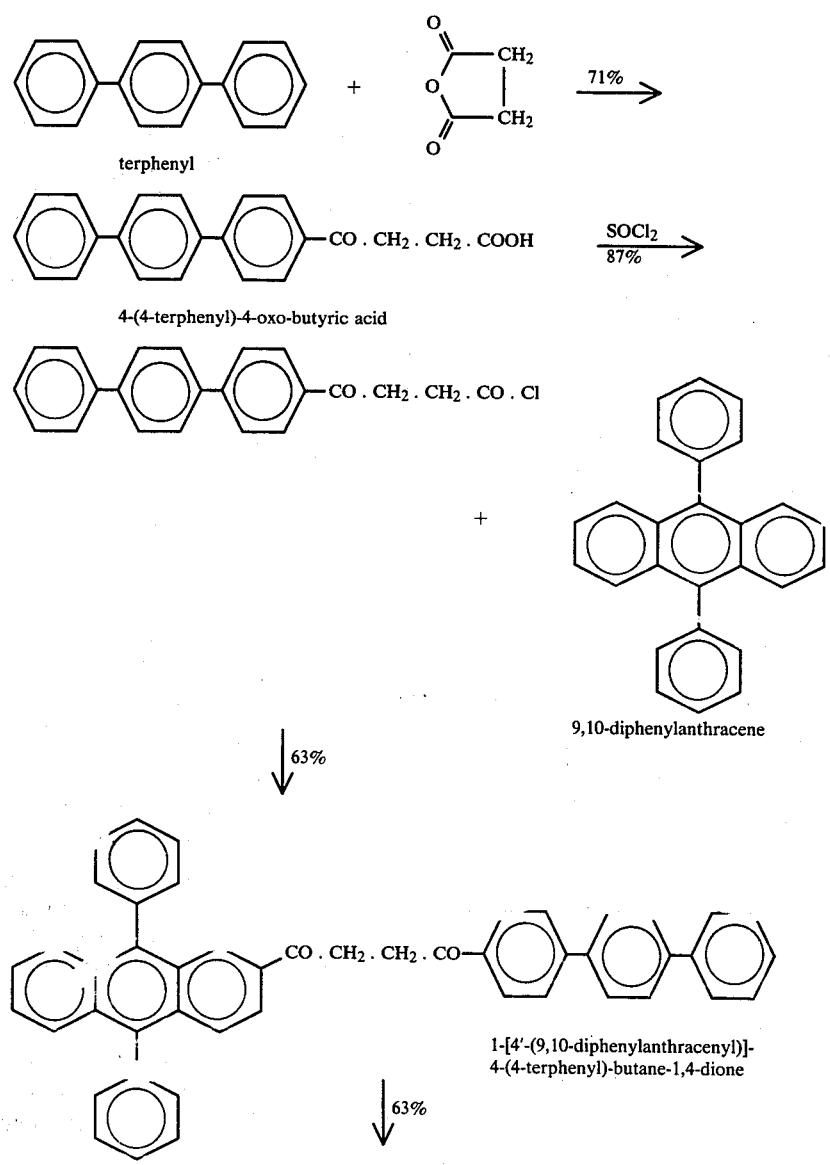

-continued

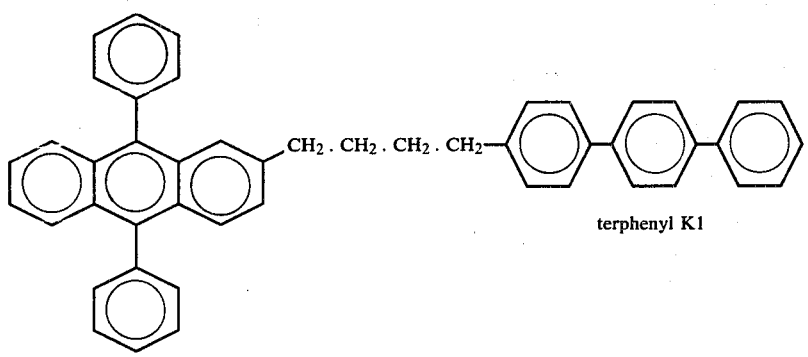

terphenyl K1

A. 4-(4-Terphenyl)-4-oxobutyric acid 45 g. (0.4 mol) aluminium chloride and 10 g. (0.1 mol) succinic anhydride are suspended in 100 ml. carbon disulphide. After cooling the mixture with ice water, a suspension of 23 g. (0.1 mol) terphenyl in 50 ml. carbon disulphide is gradually added thereto over the course of half an hour. While stirring, the reaction mixture is allowed to warm up to ambient temperature until the evolution of hydrogen chloride has ceased. The reaction mixture is left to stand for 3 hours and then poured into a mixture of ice and concentrated hydrochloric acid. The remaining solid residue is filtered off with suction and washed with water. It is subsequently dissolved in a hot aqueous solution of sodium bicarbonate, filtered and then acidified with semiconcentrated hydrochloric acid, 4-(4-terphenyl)-4-oxobutyric acid thereby precipitating out. The yield is 23 g. (71% of theory).

One equivalent of the acid is now converted into the corresponding acid chloride, using 1.5 equivalents of thionyl chloride, excess thionyl chloride being stripped off in a vacuum. The yield is 22 g. (87% of theory).

B. 1-[4'-(9,10-Diphenylanthracenyl)]-4-(4-terphenyl)-butane-1,4-dione 45 g. (0.4 mol) aluminium chloride and 19 g. (0.05 mol) of the acid chloride of 4-(4-terphenyl)-4-oxobutyric acid are suspended in 100 ml. trichloroethylene. The suspension is cooled with ice and then a suspension of 16.5 g. (0.05 mol) 9,10-diphenylanthracene in trichloroethylene gradually added thereto, the temperature not being allowed to exceed 20° C. The reaction mixture is stirred for a further hour and then left to stand for 2 hours. The reaction mixture is then poured on to about 600 g. ice and, if necessary, concentrated hydrochloric acid is added thereto. The trichloroethylene phase is separated off and the aqueous phase shaken out three times with trichloroethylene. The combined organic phases are then washed with water, with a 2% aqueous solution of sodium hydroxide and again with water. After subsequently drying with anhydrous potassium carbonate, the solvent is distilled off. The resultant 1-[2-(9,10-diphenylanthracenyl)]-4-(4-terphenyl)-butane-1,4-diol is recrystallised from o-dichlorobenzene. The yield is 20.2 g. (63% of theory).

C. 1-[4'-(9,10-Diphenylanthracenyl)]-4-(4-terphenyl)-butane (terphenyl K1)

18 g. (0.03 mol) of the above-described diketone are boiled under reflux for 2 hours with 8 g. (0.2 mol) 85% hydrazine hydrate solution and 14 g. (0.25 mol) finely powdered potassium hydroxide in 50 ml. triglycol. A mixture of hydrazine and water is then slowly distilled off until the temperature of the reaction mixture is 195° C. This temperature is maintained until the evolution of nitrogen is finished. After cooling the reaction mixture, it is diluted with water and the hydrocarbon product is extracted with diethyl ether. After stripping off the ether, the product is recrystallised from ligroin. The yield is 11.6 g. (63% of theory).

Analogous linkings were carried out with the following pairs of dyestuffs:

9,10-diphenylanthracene + 4-methoxy-terphenyl
9,10-diphenylanthracene + quaterphenyl
pyrene + terphenyl
fluorene + 4,4'''-bis-(alkyloxy)-p-quaterphenyls.

It will be understood that the specification and examples are illustrative but not limitative of the present invention and that other embodiments within the spirit and scope of the invention will suggest themselves to those skilled in the art.

What is claimed is:

1. Dyestuff comprising at least one laser dyestuff radical and at least one fluorescent dyestuff radical the fluorescent range of said fluorescent dyestuff radical overlapping the absorption range of the laser dyestuff radical and being linked with the laser dyestuff radical directly or via a bridge member having a length of at most 20 Å in such a manner that the π-electron systems of the individual laser dyestuff radical of fluorescent dyestuff radical are decoupled.

2. Dyestuff as claimed in claim 1 of the formula:

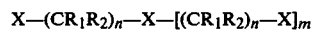

$$X-(CR_1R_2)_n-X-[(CR_1R_2)_n-X]_m$$

wherein
n is 0 or an integer from 1 up to a number corresponding to a chain length of 20 Å,
m is 0, 1, 2 or 3,
X is a laser dyestuff radical, L or a fluorescent dyestuff radical F and
$R_1$ and $R_2$, which can be the same or different, are hydrogen or alkyl of up to 6 carbon atoms,
with the provisos that one of the groups X is a laser dyestuff radical L, all the fluorescent dyestuff radical F can be the same or different and the bridge members $CR_1R_2$ can also be joined together by oxygen, nitrogen or sulfur.

3. Dyestuff as claimed in claim 1 having the formula:

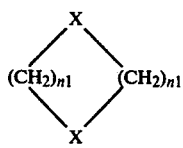

wherein
X is selected from laser and fluorescent dyestuff radical, at least one X being a laser dyestuff radical; and
n1 is a whole number from 1 to 13.

4. Dyestuff as claimed in claim 1 having the formula:

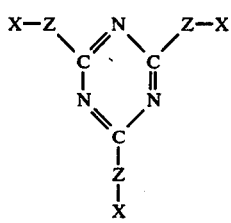

wherein
X is selected from laser and fluorescent dyestuff radical, at least one X being a laser dyestuff radical;
n1 is a whole number from 1 to 13; and
Z is oxygen or an imino (—NH—) group.

5. Dyestuff as claimed in claim 1 having the formula:

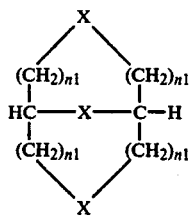

wherein
X is selected from laser and fluorescent dyestuff radical, at least one X being a laser dyestuff radical; and
n1 is a whole number from 1 to 13.

6. Dyestuff as claimed in claim 1 having the formula:

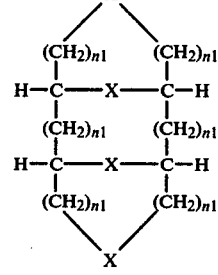

wherein
X is selected from laser and fluorescent dyestuff radical, at least one X being a laser dyestuff radical; and
n1 is a whole number from 1 to 13.

7. Dyestuff as claimed in claim 1 having the formula:

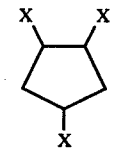

wherein
X is selected from laser and fluorescent dyestuff radical, at least one X being a laser dyestuff radical; and
n1 is a whole number from 1 to 13.

8. Dyestuff as claimed in claim 1 having the formula:

$$\text{(benzene ring with three X substituents at 1,3,5 positions)}$$

wherein
X is selected from laser and fluorescent dyestuff radical, at least one X being a laser dyestuff radical; and
n1 is a whole number from 1 to 13.

9. Dyestuff according to claim 1 having the formula:

$$HC \text{\textemdash} [(CH_2) \text{\textemdash} X]_3$$

wherein
X is selected from laser and fluorescent dyestuff radical, at least one X being a laser dyestuff radical; and
n1 is a whole number from 1 to 13.

* * * * *